US00PP29060P2

(12) United States Plant Patent
Graff

(10) Patent No.: US PP29,060 P2
(45) Date of Patent: Mar. 6, 2018

(54) ***HIBISCUS* PLANT NAMED 'HIQ 1601'**

(50) Latin Name: *Hibiscus rosa-sinensis*
Varietal Denomination: HIQ 1601

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 0 days.

(21) Appl. No.: 15/530,522

(22) Filed: Jan. 24, 2017

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hibiscus* plant named 'HIQ 1601', characterized by its upright, mounding and bushy plant habit; dark green-colored leaves; uniform and freely flowering habit; large, rich yellow-colored flowers with orange red-colored centers; and excellent flower longevity.

3 Drawing Sheets

Botanical designation: *Hibiscus rosa-sinensis.*
Cultivar denomination: 'HIQ 1601'.

BACKGROUND OF THE INVENTION

The present invention relates to a new and distinct cultivar of *Hibiscus* plant, botanically known as *Hibiscus rosa-sinensis*, and hereinafter referred to by the name 'HIQ 1601'.

The new *Hibiscus* plant is a product of a planned breeding program conducted by the Inventor in Sabro, Denmark. The objective of the breeding program is to create new strong *Hibiscus* plants with attractive and long-lasting flowers.

The new *Hibiscus* plant originated from a cross-pollination in August, 2011 in Sabro, Denmark of a proprietary selection of *Hibiscus rosa-sinensis* identified as code designation GB 2010-0107, not patented, as the female, or seed, parent with a proprietary selection of *Hibiscus rosa-sinensis* identified as code designation GB 2010-3667, not patented, as the male, or pollen, parent. The new *Hibiscus* plant was discovered and selected by the Inventor as a flowering plant within the progeny of the stated cross-pollination in a controlled greenhouse environment in Sabro, Denmark in May, 2012.

Asexual reproduction of the new *Hibiscus* plant by vegetative terminal cuttings in a controlled greenhouse environment in Sabro, Denmark since September, 2012 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIQ 1601'. These characteristics in combination distinguish 'HIQ 1601' as a new and distinct *Hibiscus* plant:

1. Upright, mounding and bushy plant habit.
2. Dark green-colored leaves.
3. Uniform and freely flowering habit.
4. Large, rich yellow-colored flowers with orange red-colored centers.
5. Excellent flower longevity.

Plants of the new *Hibiscus* can be compared to plants of the female parent selection. Plants of the new *Hibiscus* differ primarily from plants of the female parent selection in the following characteristics:

1. Flowers of plants of the new *Hibiscus* are longer-lasting than flowers of plants of the female parent selection.
2. Plants of the new *Hibiscus* have better garden performance than plants of the female parent selection.

Plants of the new *Hibiscus* can be compared to plants of the male parent selection. Plants of the new *Hibiscus* differ primarily from plants of the male parent selection in the following characteristics:

1. Leaves of plants of the new *Hibiscus* are glossier than leaves of plants of the male parent selection.
2. Flowers of plants of the new *Hibiscus* are longer-lasting than flowers of plants of the male parent selection.

Plants of the new *Hibiscus* can be compared to plants of the *Hibiscus rosa-sinensis* 'Adonis Yellow', disclosed in U.S. Plant Pat. No. 26,006. In side-by-side comparisons, plants of the new *Hibiscus* differ from plants of 'Adonis Yellow' in the following characteristics:

1. Leaves of plants of the new *Hibiscus* are glossier than leaves of plants of 'Adonis Yellow'.
2. Plants of the new *Hibiscus* and 'Adonis Yellow' differ slightly in flower color as plants of 'Adonis Yellow' have lighter yellow-colored flowers.
3. Plants of the new *Hibiscus* have better garden performance than plants of 'Adonis Yellow'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet is a side perspective view of a typical flowering plant of 'HIQ 1601' grown in a container.

The photograph on the second sheet is a close-up view of typical developing flower buds and a typical open flower of 'HIQ 1601'.

The photograph on the third sheet is a close-up view of a typical dissected flower of 'HIQ 1601' showing the upper surfaces of the petals.

DETAILED BOTANICAL DESCRIPTION

The aforementioned photographs and following observations, measurements and values describe plants grown during the autumn in 13-cm containers in a glass-covered greenhouse in Sabro, Denmark and under cultural practices typical of commercial *Hibiscus* production. During the production of the plants, day temperatures ranged from 20° C. to 25° C., night temperatures ranged from 19° C. to 21° C. and light levels ranged from 40 to 50 klux. Plants were pinched one time nine weeks after planting and plants were 26 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'HIQ 1601'.

Parentage:

- *Female, or seed, parent*.—Proprietary selection of *Hibiscus rosa-sinensis* identified as code number GB 2010-0107, not patented.
- *Male or pollen parent*.—Proprietary selection of *Hibiscus rosa-sinensis* identified as code number GB 2010-3667, not patented.

Propagation:

- *Type*.—By vegetative terminal cuttings.
- *Time to initiate roots, summer*.—About three weeks at ambient and soil temperatures about 24° C.
- *Time to initiate roots, winter*.—About four weeks at ambient and soil temperatures about 24° C.
- *Time to produce a rooted young plant, summer*.—About eight weeks at ambient and soil temperatures about 24° C.
- *Time to produce a rooted young plant, winter*.—About ten weeks at ambient and soil temperatures about 24° C.
- *Root description*.—Medium in thickness, fleshy; color, close to 158A, actual color of the roots is dependent on substrate composition, water quality, fertilizer type and formulation, substrate temperature and physiological age of roots.
- *Rooting habit*.—Freely branching; dense.

Plant description:

- *Plant and growth habit*.—Container plant; upright, mounding and bushy plant habit; moderately vigorous growth habit.
- *Branching habit*.—Freely branching habit with usually about four to seven primary branches each with about five to seven secondary branches developing per plant; pinching enhances lateral branch development.
- *Plant height, soil level to top of foliar plane*.—About 23 cm to 43 cm.
- *Plant height, soil level to top of floral plane*.—About 25 cm to 45 cm.
- *Plant diameter* (*area of spread*).—About 30 cm to 50 cm.

Lateral branch description:

- *Length*.—About 12 cm to 20 cm.
- *Diameter*.—About 5 mm to 7 mm.
- *Internode length*.—About 1 cm to 5 cm.
- *Strength*.—Strong.
- *Texture*.—Smooth, glabrous; becoming woody with development.
- *Luster*.—Semi-glossy.
- *Color, developing*.—Close to 147B; color becoming closer to 147A with development; at the internodes, close to 137A.
- *Color, developed*.—Close to between N199A and 197A.

Leaf description:

- *Arrangement*.—Alternate, single; numerous.
- *Length*.—About 6 cm to 10 cm.
- *Width*.—About 4.5 cm to 7 cm.
- *Shape*.—Obovate.
- *Apex*.—Acuminate.
- *Base*.—Obtuse.
- *Margin*.—Irregularly serrate.
- *Texture, upper surface*.—Smooth, glabrous.
- *Texture, lower surface*.—Scattered pubescence; venation prominent.
- *Luster, upper and lower surfaces*.—Slightly glossy.
- *Venation pattern*.—Pinnate; arcuate.
- *Color*.—Developing leaves, upper surface: Close to 137A. Developing leaves, lower surface: Close to 138A. Fully expanded leaves, upper surface: Close to N189A; venation, close to 132A. Fully expanded leaves, lower surface: Close to N138B; venation, close to 138B.
- *Petioles*.—Length: About 1.5 cm to 4 cm. Diameter: About 2 mm. Texture, upper and lower surfaces: Smooth, glabrous. Luster, upper and lower surfaces: Slightly glossy. Color, upper surface: Close to 152A. Color, lower surface: Close to 138A.
- *Leaf stipules*.—Quantity and arrangement: Two at the base of the petiole, opposite. Length: About 5 mm. Diameter: About 1 mm. Shape: Lanceolate. Color, upper and lower surfaces: Close to 137A.

Flower description:

- *Flower arrangement*.—Flowers arranged singly at terminal leaf axils; uniform, continuous and freely flowering habit with numerous flowers developing per plant; flowers face mostly upright to slightly outwardly.
- *Fragrance*.—None detected.
- *Natural flowering season*.—Plants flower in the garden during the spring and summer or during periods of warm weather; in the greenhouse, plants can be flowered year-round; plants begin flowering about 10 to 13 weeks after pinching.
- *Flower longevity*.—Excellent flower longevity, flowers last for about four to five days; flowers persistent.
- *Flower diameter*.—About 13 cm to 19 cm.

*Flower length* (*height*).—About 10 cm to 11 cm.

*Flower buds*.—Rate of opening: Flowers buds open in about three days. Length: About 5 cm to 7 cm. Diameter: About 2 cm to 3 cm. Shape: Ovoid to elliptical. Color: Close to 1B.

*Petals*.—Arrangement: Five petals in a single whorl; petals imbricate. Length: About 9 cm to 10 cm. Width: About 7 cm to 9 cm. Shape: Fan-shaped. Apex: Rounded. Base: Attenuate. Margin: Entire; moderately undulate. Texture, upper surface: Glabrous; rough with a velvety appearance. Texture, lower surface: Glabrous, rough with a satiny appearance. Luster, upper surface: Matte. Luster, lower surface: Moderately glossy. Color: When opening, upper surface: Close to 13B; towards the base, close to 34A. When opening, lower surface: Close to 11B. Fully opened, upper surface: Close to 13A; towards the base, close to 34A; with development, main color becoming closer to 12B and towards the base, close to 34A; venation, close to 15A. Fully opened, lower surface: Close to 11B; with development, color becoming closer to 8C; venation, close to 15A.

*Sepals*.—Appearance: Five sepals fused into a campanulate-shaped calyx. Length: About 3 cm to 3.3 cm. Width: About 1 cm to 1.5 cm. Shape: Lanceolate. Apex: Acuminate. Margin: Entire. Texture, upper surface: Glabrous, rough. Texture, lower surface: Glabrous, smooth. Luster, upper and lower surfaces: Matte. Color, upper surface: Close to 141B. Color, lower surface: Close to 144A.

*Involucral bracts*.—Quantity and arrangement: About seven or eight in a single whorl subtending the calyx and forming a star-shaped epicalyx. Length: About 1 cm to 1.5 cm. Diameter: About 2 mm to 5 mm. Shape: Lanceolate. Apex: Acute. Margin: Entire. Texture, upper and lower surfaces: Rough, glabrous. Color, upper and lower surfaces: Close to 141A.

*Peduncles*.—Length: About 4 cm to 6 cm. Diameter: About 2 mm to 4 mm. Strength: Strong. Aspect: Mostly upright. Texture: Sparsely pubescent. Luster: Slightly glossy. Color: Close to 143A.

*Reproductive organs*.—Androecium: Stamen number: Numerous, more than 100. Filament length: About 5 mm to 10 mm. Filament color: Close to 13A. Anther shape: Rounded to ovate. Anther length: About 1 mm to 2 mm. Anther color: Close to 19A. Amount of pollen: Abundant. Pollen color: Close to 17A. Gynoecium: Pistil length: About 7 cm to 9 cm. Staminal column texture: Smooth, waxy. Staminal column color: Towards the base, close to N30A; mid-section, close to 28A; towards the apex, close to 15B. Style length: Five-parted, about 4 mm to 5 mm. Style color: Close to 4B. Stigma appearance: Five rounded stigma pads. Stigma pad color: Close to 26A. Ovary color: Close to 149D.

*Seeds*.—Quantity per fruit: Typically, about 1 to 15 develop. Length: About 5 mm. Diameter: About 5 mm. Texture: Rough. Color: Close to 202A.

*Fruits*.—Quantity per flower: One. Length: About 2 cm to 3 cm. Diameter: About 1 cm to 2 cm. Texture: Smooth, leathery. Color: Close to 138A or 145A.

Temperature tolerance: Plants of the new *Hibiscus* have been observed to have tolerate temperatures from about 10° C. to about 40° C.

Pathogen & pest resistance: Plants of the new *Hibiscus* not been observed to be resistant to pathogens and pests common to *Hibiscus* plants.

It is claimed:

1. A new and distinct *Hibiscus* plant named 'HIQ 1601' as illustrated and described.

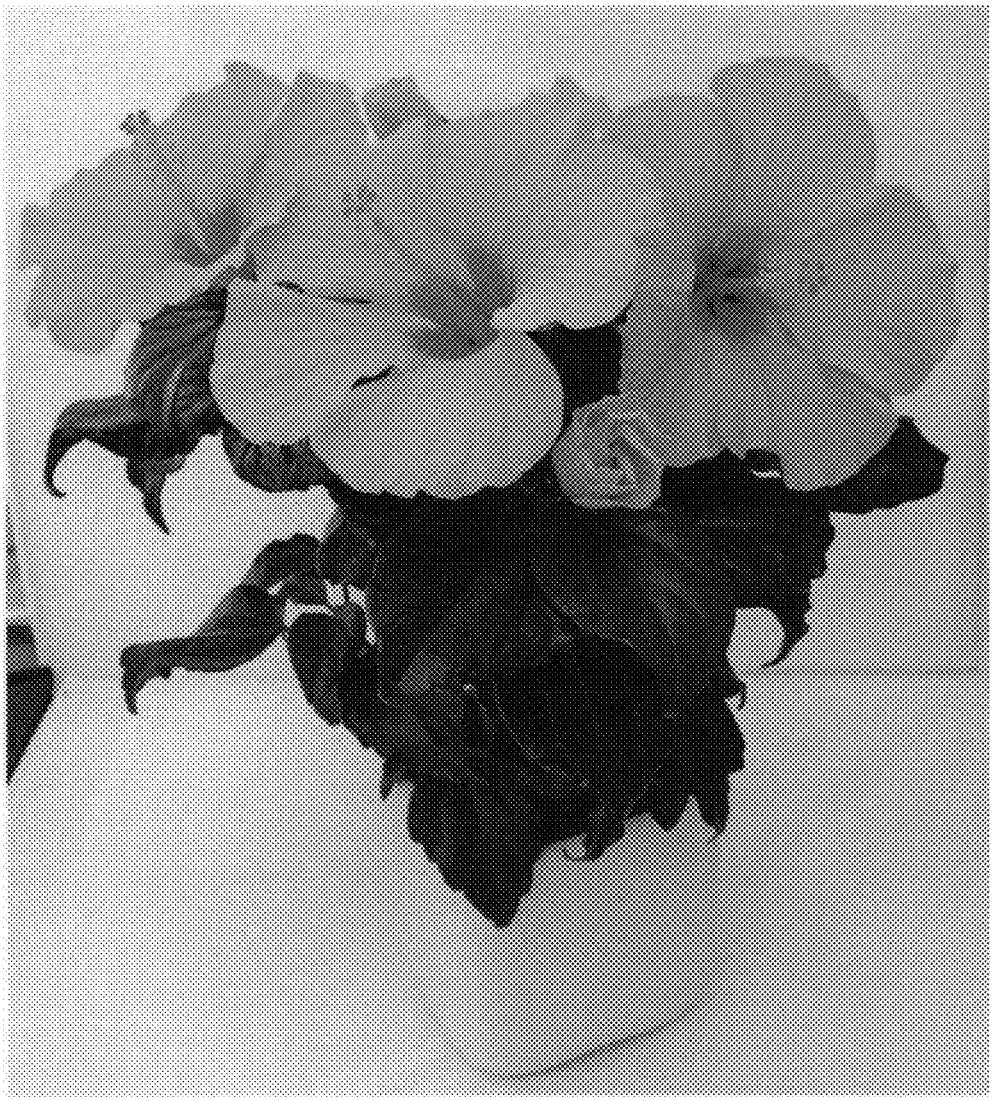

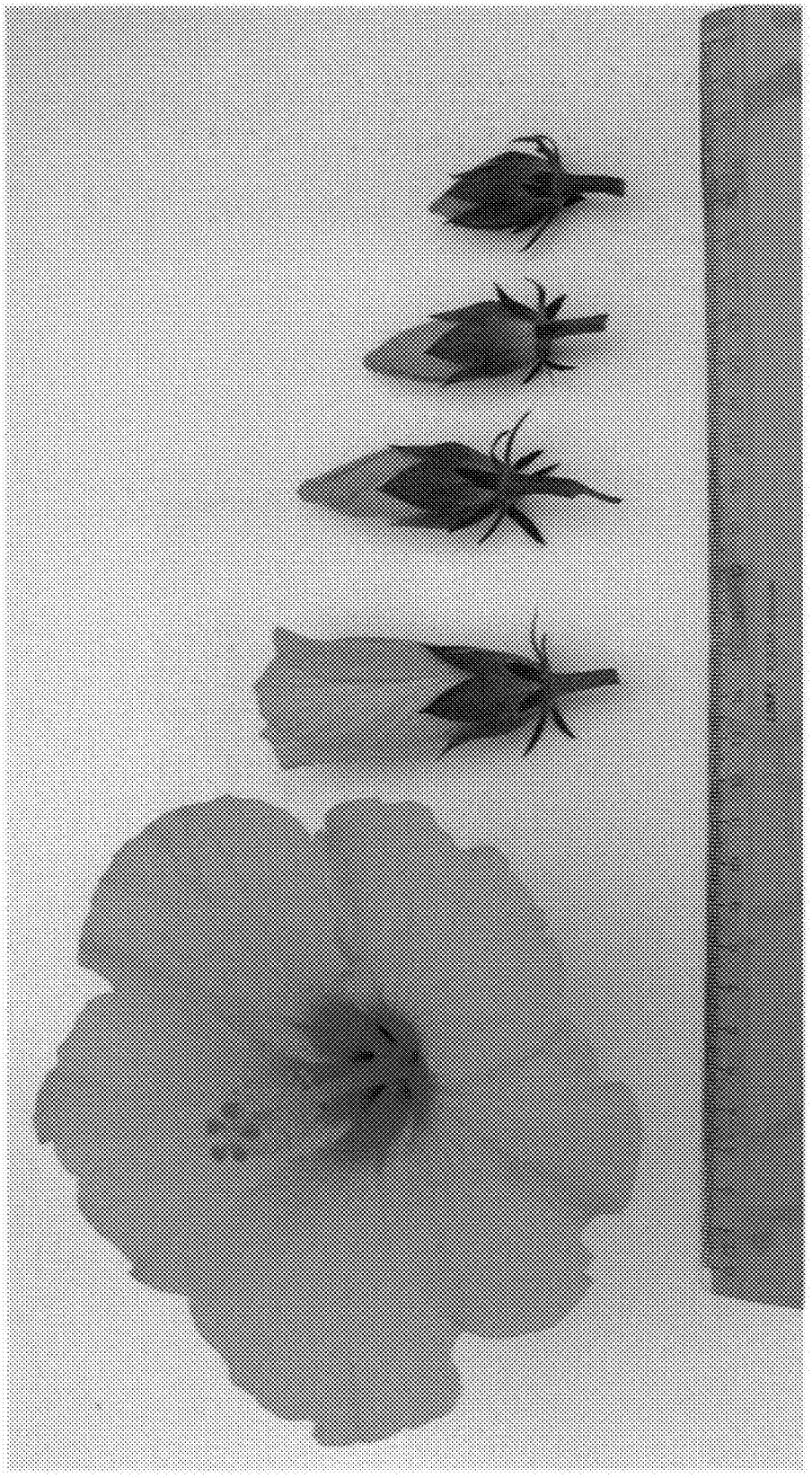

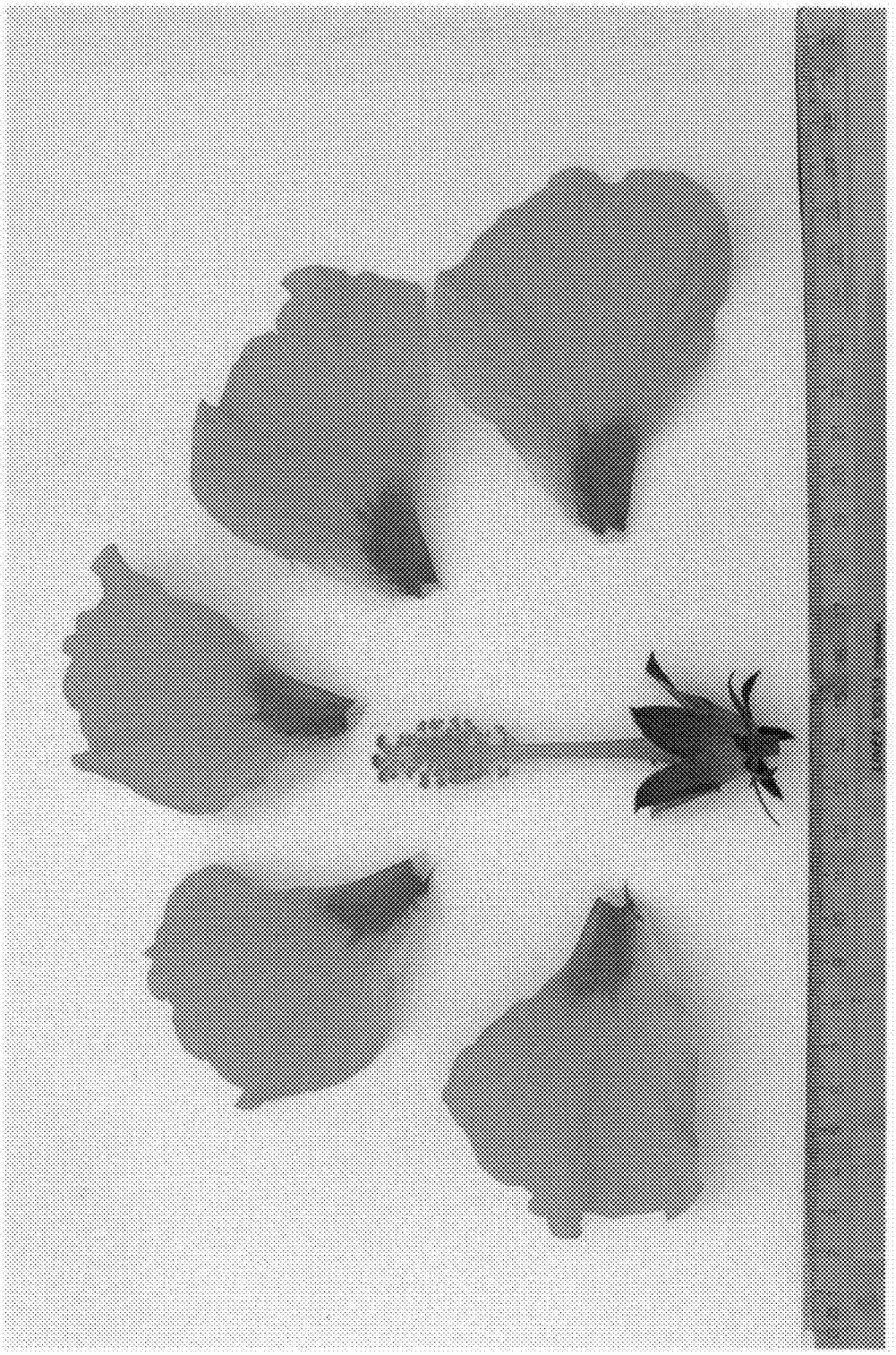

* * * * *